(12) United States Patent
Wang et al.

(10) Patent No.: US 7,235,077 B1
(45) Date of Patent: Jun. 26, 2007

(54) BONE FIXATION DEVICE AND METHOD

(75) Inventors: Robert Wang, Las Vegas, NV (US); Mohamed B. Trabia, Las Vegas, NV (US)

(73) Assignee: Board of Regents of the University and Community College System of Nevada on behalf of the University of Nevada, Reno, Reno, NV (US)

( * ) Notice: Subject to any disclaimer, the term of this patent is extended or adjusted under 35 U.S.C. 154(b) by 288 days.

(21) Appl. No.: 10/293,732

(22) Filed: Nov. 12, 2002

Related U.S. Application Data

(60) Provisional application No. 60/350,785, filed on Nov. 9, 2001.

(51) Int. Cl.
*A61B 17/58* (2006.01)
(52) U.S. Cl. ...................................................... 606/69
(58) Field of Classification Search ................. 606/69, 606/70, 71
See application file for complete search history.

(56) References Cited

U.S. PATENT DOCUMENTS

| | | | |
|---|---|---|---|
| 5,290,281 A | | 3/1994 | Tschakaloff |
| 5,807,382 A | * | 9/1998 | Chin ............................ 606/53 |
| 5,855,580 A | * | 1/1999 | Kreidler et al. ................ 606/71 |
| 5,947,970 A | | 9/1999 | Schmelzeisen et al. |
| 6,004,353 A | * | 12/1999 | Masini ..................... 623/22.21 |
| 6,060,641 A | | 5/2000 | Manolidis |
| 6,302,884 B1 | | 10/2001 | Wellisz et al. |
| 6,368,326 B1 | * | 4/2002 | Dakin et al. ................. 606/103 |
| 6,423,068 B1 | * | 7/2002 | Reisberg et al. ............... 606/69 |
| 6,423,069 B1 | | 7/2002 | Sellers |

FOREIGN PATENT DOCUMENTS

EP   291632 A1 * 11/1988

OTHER PUBLICATIONS

Haug, RH, et al, "A Biomechanical Evaluation of Mandibular Angle Fracture Plating Techniques", Journal of Maxillofac Surg, Oct. 2001, 2 pages, www.ncbi.nlm.nih.gov.
Wang, Robert C., et al, A Simple, Effective Means of Mandibular Fixation, pp. 448-452, Apr. 1998, Archotolaryngol Head Neck Surg/vol.124.

(Continued)

*Primary Examiner*—Eduardo C. Robert
*Assistant Examiner*—James L. Swiger
(74) *Attorney, Agent, or Firm*—Cyr & Associates, P.A.

(57) ABSTRACT

An apparatus and method of reducing and fixating bone fragments during osteosynthesis is disclosed. An internal fixation plate has first and second arms forming an acute angle. Attachment locations adapted to secure the plate to bone are located at distal portions of the respective arms. A third attachment location is located intermediate the first and second attachment locations. The arms have both a rigid retainer portion to assist in aligning opposing bone fragments and a flexible portion that desirably conforms to the surface of the bone to which it is to be fastened without requiring a surgeon to attempt to bend the plate prior to fastening it to the bone. A method is described for using the plate in combination with a tension-wire method that uses monocortical screws with stainless-steel wire to reduce and fixate a fracture.

1 Claim, 12 Drawing Sheets

OTHER PUBLICATIONS

Tate, Gregory, S, et al, "Bite Forces in Patients Treated for Mandibular Angle Fractrures" 1994, pp. 734-736, J Oral Maxillofac Surg. 52.

Kroon, Frans H.M., et al, "The Use of Miniplates in Mandibular Fractures", pp. 199-204, 1991, J. Cranio-Max.-Fac. Surg. 19.

Trabia, Mohamed S., et al, "Design of a V-Plate-Wire Fixation System for a Mandibles" 2001, 2 pages, Advances in Bioengineering, Bed-vol. 51.

Champy, Maxime, et al, "Mandibular Osteosynthesis by Miniature Screwed Plates Via a Buccal Approach", 1978, pp. 14-21, J.Max-Fac. Surg. 6.

Shetty, Vivak, et al, "Fracture Line Stability as a Function of the Internal Fixation System: As In Vitro Comparision Using a Mandibule Angle Fracture Model", Journal of pp. 791-801, 1995, Journal of Maxilofac Surg. 53.

Trabia, Mohamed S., et al, "Design of a V-plate Wire Mandibular Fixation System", 2001, 2 pages. ASME International Mechanical Engineering Congress and Exposition Nov. 11-16, 2001, NY, NY.

Wang, Robert C., et al, "The Tension Wire Method—A Simple, Effective Means of Mandibular Fixation", pp. 448-452, Apr. 1996, Archtolaryngol Head Neck Surg/vol. 124 [*document previously cited with the listed as A Simple, Effective . . . ).

* cited by examiner

BONE FIXATION DEVICE AND METHOD

CROSS-REFERENCE TO RELATED APPLICATIONS

Application claims the benefit of U.S. Provisional Application 60/350,785 filed Nov. 9, 2001 entitled V-Plate-Wire Mandible Fixation System.

BACKGROUND

Mandible fractures are common facial injuries, which can occur following severe impacts such as those experienced in motor vehicle accidents and sports. Repair of mandibular fractures first requires bringing the fragments into their correct anatomical position (reduction) and appropriate alignment of the fracture segments so that they can be immobilized (fixated) during fracture healing. When these two goals can be accomplished efficiently and with minimal tissue disruption, the risk of malunion and infection are reduced.

The mandible has an outer surface that is called the outer cortex. Even though this cortical surface is fractured, the bone fragments may not move relative to each other. In general, if the fragments do not move, they are considered stable (or favorable) and are usually managed with conservative techniques, including wiring the upper jaw and the mandible together (intermaxillary fixation or "IMF") to maintain their pre-existing or normal dental occlusion (the way upper and lower teeth meet). When one of the fragments moves towards the cheek or lips (buccal-labial movement), or towards the tongue (lingual movement), it is unstable (or unfavorable) and surgical methods of open reduction/internal fixation (ORIF) must be considered. Treatment of mandibular fractures using an ORIF technique generally proceeds by first performing IMF and then reducing the fractured bone, and then securing (fixating) the bone in place.

Depending upon the anatomic location and the specific characteristics of the fracture site 100, best seen in FIG. 1, fixation is accomplished through a variety of techniques including drilling holes through the bone and wiring them together (interosseous wiring) (not shown) or by using plates. An internal fixation plate 98 is generally a flat, elongated section of rigid metal containing screw holes at various points along its length for receiving screws to fasten the plate to the bone. One or more plates are placed across a fracture line 100 to fix the bone mass on both sides of the fracture to each other. The plates are secured to the bone with fasteners, usually screws. Interosseous wiring is simple, inexpensive, and needs less exposure of the tissue than that required for plate fixation techniques. It can also reduce and fixate the fracture, but this repair is non-rigid and tends to loosen because of the pressure the thin wire threaded through the bone exerts on the comparatively soft cortical bone. Because the forces the patient exerts when chewing (mastication) exceed the elastic limits of the interosseous wires, this technique not only requires the contemporaneous use of IMF during surgery (as is also done with plating) but also for as long as 6 weeks after surgery. Plate systems, however, can often be used without IMF after surgery.

To facilitate bone fracture healing (osteosynthesis), these fixation systems typically employ metallic hardware, including plate and screws, formed of biocompatible, corrosion resistant metals such as titanium and stainless steel. Systems utilizing resorbable materials have also recently been introduced.

While the main advantage of metallic plates is that they are strong and provide rigid stabilization of the fragments during osteosynthesis, they possess a number of inherent shortcomings. First, in order to accomplish reduction of the fragments, the surgeon must bring the bone fragments into proper alignment. This procedure usually requires the use of a surgical assistant who brings the fragments into alignment and then holds them in position either manually, or with a special tool. Second, because the surface of the mandible is not completely flat, the surgeon typically uses instruments to twist, bend and attempt to conform the conventional flat metal plate to the portion of the mandible onto which it is to be affixed. Shaping and re-shaping the rigid metal plates to conform adequately to bone surfaces is largely accomplished through trial and error. This method, usually conducted while the patient is under anesthesia, increases the requirements for anesthesia and operating room time. If the plate is not shaped correctly to conform to the bone surface, the rigid plate creates an additional problem because during osteosynthesis, bony fragments conform to the plate forcing the bone to heal in an anatomically incorrect position, which may result in dental malocclusion (errors in the way the upper and lower teeth meet to chew food).

Some conventional internal fixation plates have a compression feature that uses the force exerted by tightening the screw in the eccentrically shaped hole through the plate to force the fragments together. When this plate is used, a drill bit is used to drill a hole at the outer edge of the (eccentric compression) hole. A screw is then inserted into the hole and tightened enough to hold the plate in approximate position over the fracture site. The surgeon then turns his attention to the opposite fragment and repeats the procedure by drilling another hole to the outside of the opposite (eccentric compression) hole. The two screws are tightened to obtain compression of the fragments. Two additional screws are then placed through the holes in the outer portion of the plate and the system is stabilized. This technique is not very forgiving. Over or under compression of the fragments can cause displacement. If the mandible is inaccurately positioned, malunion or malocclusion may result. To prevent this undesirable, result, the plate may have to be reapplied in a new position.

Conventional rigid internal fixation plating techniques can also increase the opportunity for complications. For example, the exposure necessary for insertion of large plates can devascularize cortical (outer layer of) bony fragments. Plating on both sides of the mandible (bicortical), also risks injury to the inferior alveolar neurovascular bundle. While rigid plates may effectively restrain the opposing bone fragments against relative movement, as is required to achieve osteosynthesis, when they are not properly positioned, that same rigidity may contribute to bony deformation and malunion.

Rigid fixation of unstable, distracted mandibular fractures is often associated with a "catch-22" problem that requires accurate reduction to fixate while simultaneously needing some method of temporarily fixating the fragments in reduction in order to apply the chosen rigid fixation.

A tension-wire method that uses monocortical screws with stainless-steel wire for fracture reduction and fixation in conjunction with intermaxillary fixation has been described in Wang et al., Arch. Otolaryngol. Head Neck Surg. 124 (April 1998)448-452. In Wang, two screw holes for 2.0-mm-diameters self-tapping titanium or stainless-steel screws, 4 or 6 mm in length, are placed perpendicular to and on each side of the fracture line. Monocortical screws are placed approximately 4 to 6 mm from the fracture line. The screws are then tightened down and then reversed 2 turns to allow a 24-gauge stainless-steel wire loop to be passed around them and fit underneath the head of the first screw. The wire loop, which is tightened around the two screws, both reduces and fixates the opposing sides of the fractured bone. Because the head of the screws are conical, tightening the screws results in further reduction of the fragments.

While the above described tension-wire method (TWM) was originally devised as a method of temporary reduction for rigid fixation, it has been found to be a stable and effective method of fixation. When compared to methods utilizing miniplates, or dynamic compression plates, the TWM also requires less dissection and exposure of the tissues than that required for plating or lag screw techniques, and it is applicable to most simple fractures of the parasymphysis, body, angle, and ramus without the need for external incisions. TWM reduces and fixates the fracture simultaneously and can also be used to reduce an unstable fracture. The TWM is quite strong when two or more planes of fixation can be achieved. Other screw and wire loops can be added to adjust reduction. Despite its advantages, one disadvantage of the TWM alone, which is not encountered with plate and lag screw rigid fixation devices, is the concurrent need for use of IMF, which precludes immediate oral rehabilitation. Because IMF generally supplements the TWM, it should not be used where IMF is contraindicated, such as elderly, debilitated patients and those with increased nutritional demands for whom early oral rehabilitation is important.

Finite element analysis of TWM demonstrates that because the wire is usually plastically deformed while being tightened, it suffers from lack of strength to support biting forces (mastication) during the period of fracture healing. Since IMF must generally supplement TWM, the patient's jaw is required to remain wired for several weeks after the ORIF. While plating devices could be used in conjunction with TWM to dispense with IMF postoperatively, that technique would not solve the problems associated with the use of rigid metal plates.

The TWM is comparatively quick and easy to use because it simultaneously combines reduction and fixation, does not increase the complication rate, and has a low cost. This makes TWM an attractive alternative to current methods of mandibular internal reduction and fixation for simple and/or unstable fractures. In order to meet all the goals of mandibular fracture repair however, and reduce the problems encountered with existing internal fixation techniques using metal plates, utilize the benefits of TWM, and eliminate the need for IMF after surgery, a new device is desirable.

SUMMARY

An embodiment in accordance with the present invention is disclosed that provides an internal fixation plate having both a rigid retainer portion to assist in aligning opposing bone fragments and a flexible portion that will desirably conform to the cortical surface of the bone to which it is to be fastened without requiring the surgeon to attempt to bend the plate prior to fastening it to the bone.

An embodiment in accordance with the present invention includes a base having two non-linear arms, three fastener portions wherein two fastener portions are disposed along each arm and one fastener portion that is intermediate to the two other fastener portions. Each arm of the base contains a flexible portion and a retainer portion. The flexible portion of each arm is designed to allow the base to desirably conform to the surface of the bone. To assist in alignment and fixing the two sides of the fracture, the retainer portion is placed across the fracture line and against the two bone fragments. The intermediate fastener portion is fastened to the bone on one side of the non-comminuted, or simple fracture line and the non-intermediate fastener portions are fastened to the bone on the second side of the fracture line.

In particular, some embodiments use screws inserted through an aperture in a fastener portion to fasten the base to the bone. In one embodiment, one of the fastener portions includes a shelf that is adapted to slideably retain a base the surgeon slides under a previously placed screw. This channel eliminates the surgeon's need to align the base with the hole in the bone and insert a screw through a hole in the base. A base so engaged, may be released by sliding the shelf out from under the screw that is secured to the bone. An embodiment of the base is designed to be subcutaneously implanted and remain affixed to the bone fragments.

In some embodiments, the base can be used alone in a manner similar to use of a conventional internal fixation plate, where the surgeon manually reduces and aligns the fracture. Other embodiments are designed to allow the surgeon to use the benefits of the tension wire method to reduce and fixate the bone fragments and to obtain the benefits of the base. In such embodiments, two screw holes are placed normal to the line of the fracture, a screw is inserted into each one of each hole and the screws are tightened and then loosened slightly, to allow the shelf of the base to be slid under a first screw. The screw is tightened, thereby temporarily securing the base to the bone. A wire is then placed around a channel in the base and around the second screw. In this embodiment, the wire channel allows the surgeon to use the benefits of the tension wire method in combination with the benefits of the base by keeping the wire against the bony cortex to minimize undesirable moment forces upon the bony fragments. The wire is then tightened around the channel and around the base until the fracture fragments are properly aligned and apposed, and the second screw tightened.

A method in accordance with an embodiment of the present invention for treating a fracture of the mandible generally comprises the following steps: Making an incision to access the repair site; reducing and fixating the fracture using the TWM; drilling additional holes through the apertures in the distal fastener portions of the base and into the bone; inserting screws through the apertures in the base and fastening the flexible arms of the base to the bone.

BRIEF DESCRIPTION OF THE DRAWINGS

The present invention is described with respect to particular exemplary embodiments thereof and reference is accordingly made to the drawings (which are not necessarily drawn to scale) in which.

DETAILED DESCRIPTION

The device of the present invention is discussed herein with reference to an embodiment to be used to fixate fragments of a fracture of the body of the mandible in their anatomically correct positions. It will be apparent however, that such a device is not limited to fractures of the body of the mandible, or to fractures of the mandible generally, but finds general application for internal fixation of fractures of other bones of the skeleton.

Figure 1:
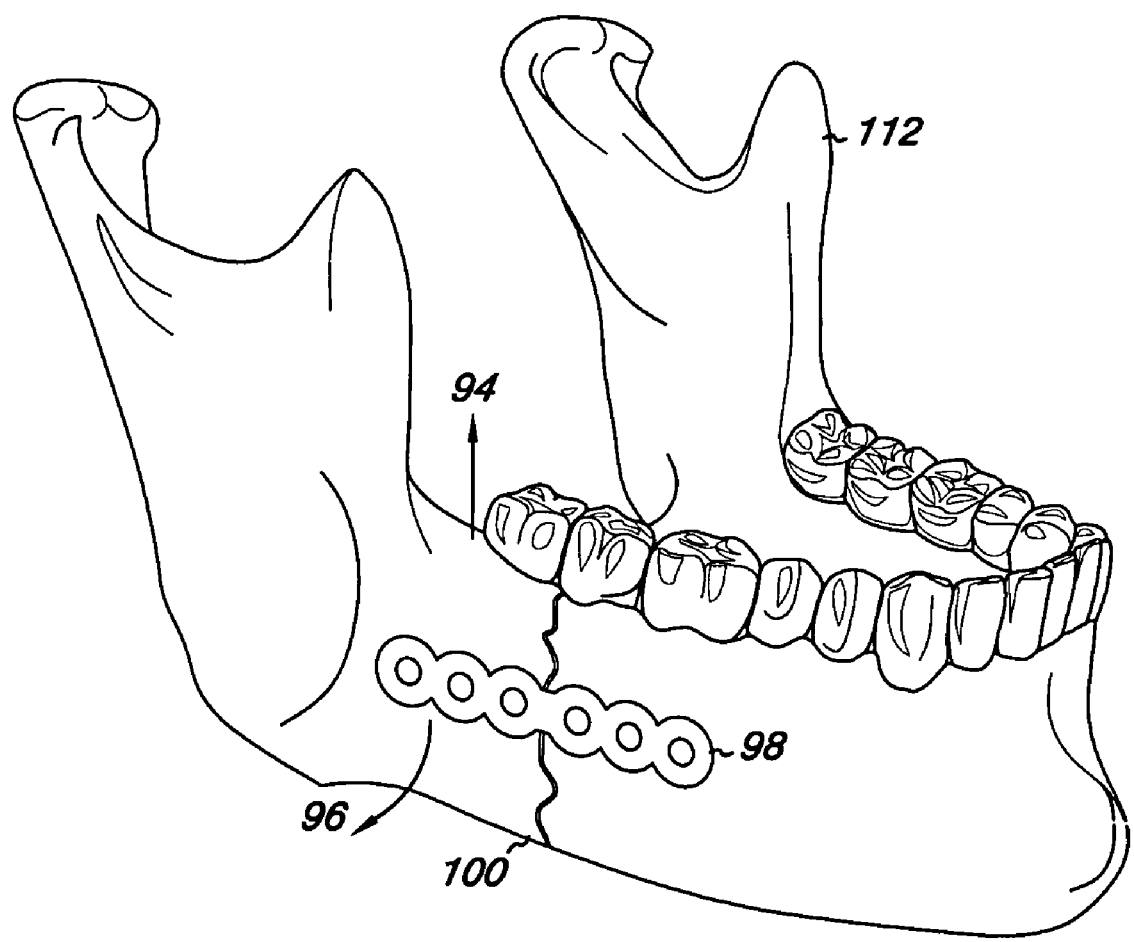
FIG. 1 is a 3-dimensional view showing a fracture of the body of the mandible, and a typical conventional base.

FIG. 1 illustrates the general anatomical areas of a mandible 112. A typical conventional plate 98 is shown affixed to a fracture line 100, here shown in the body of mandible 112. If a fragment of the fracture moves towards the cheek or lips in the direction of arrow 96, the fracture fragment is said to have moved in the buccal-labial direction. If a fragment of the fracture moves toward the tongue, i.e., in the direction of arrow 94, it is said to have moved in the lingual direction. In practice, when a base, e.g., 100, is affixed to the surface of a mandible 112 in the manner shown in FIG. 1, the surface of the base 100 that is seen in that view faces away from the surface of the bone and towards the soft tissues of the cheeks. Here, we define the surface of a base 100 seen in FIG. 1 to be the "buccal-labial" surface.

Figure 2:
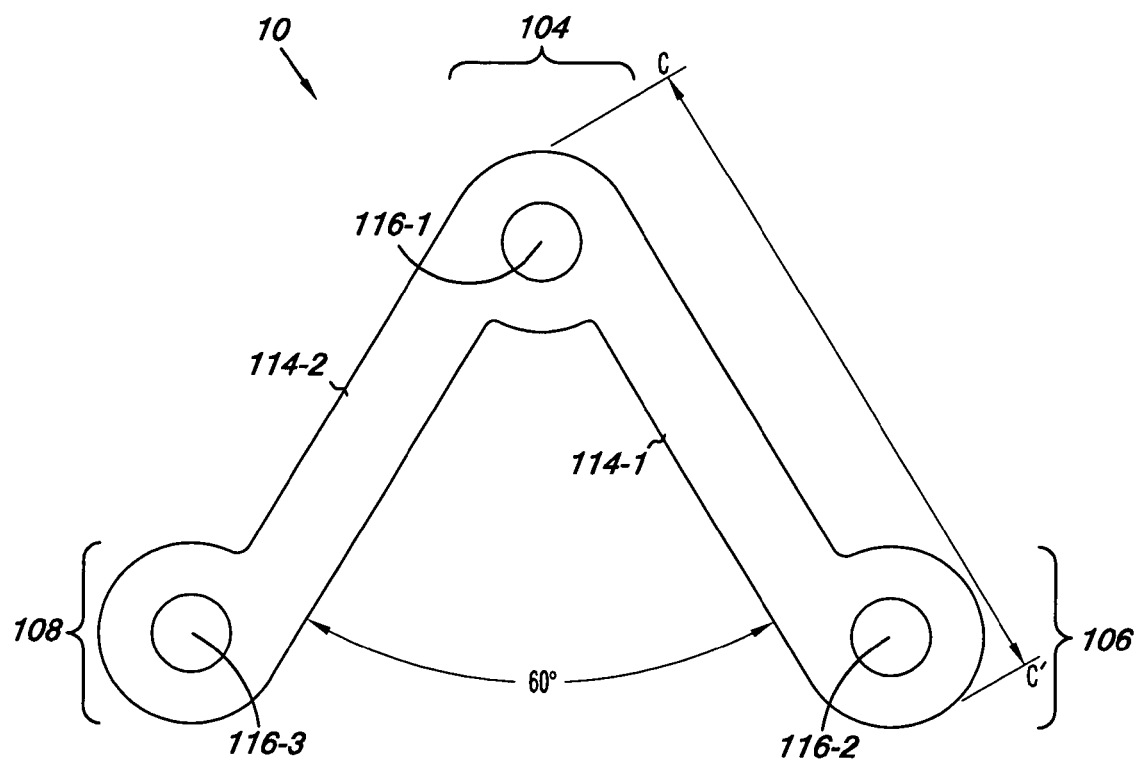
FIG. 2 is a top view of a base according to and embodiment of the invention.
Figure 2A:
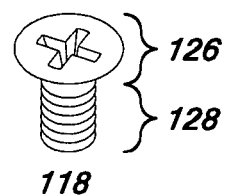
FIG. 2A illustrates a typical bone screw.
Figure 3:
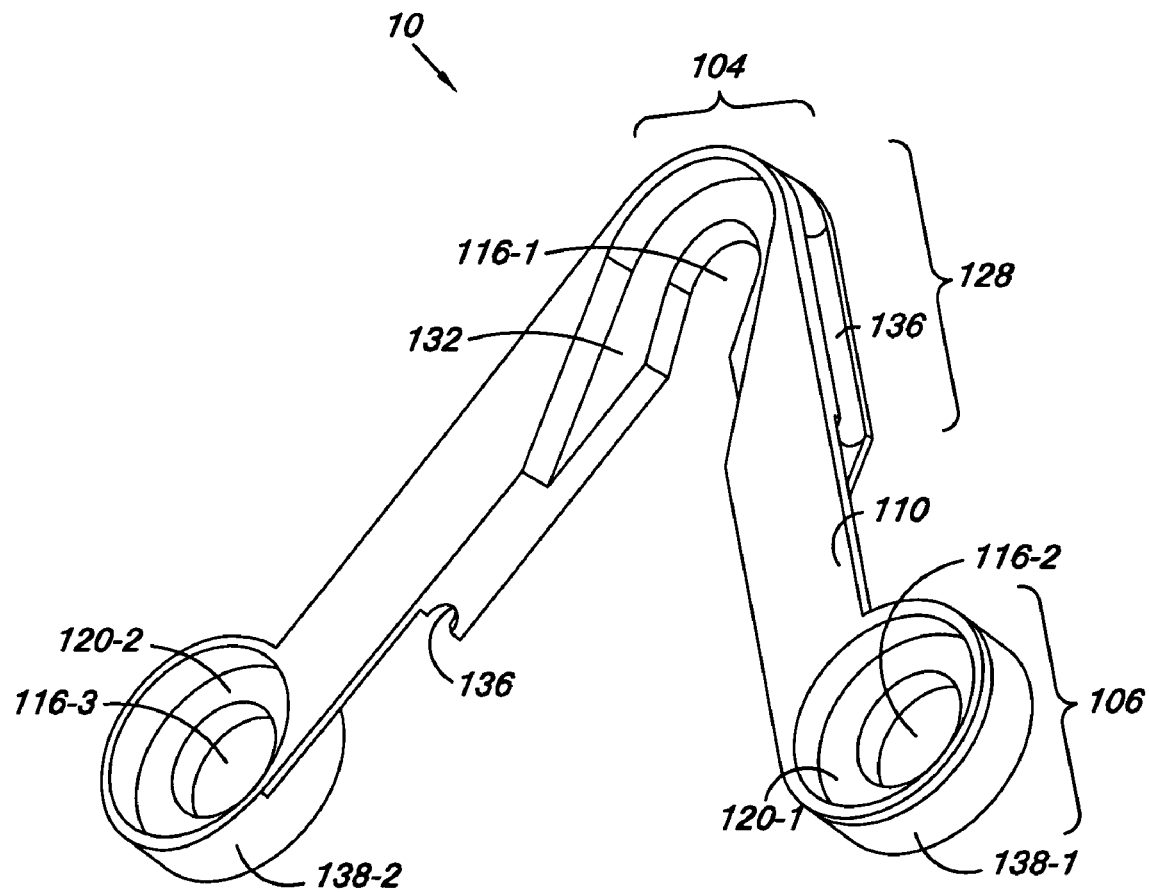
FIG. 3 is a top perspective (labial side) view of an embodiment of the invention.

FIGS. 2-3, illustrate an embodiment of the invention, in which a base 10 comprised of two non-linear arms 114-1 and 114-2, each of which extends forwardly from an intermediate fastener portion or attachment location 104 and towards the distal fastener portions or attachment locations 106 and 108 respectively. The non-linear arms 114-1 and 114-2 are disposed about an intermediate fastener portion 104. Each arm 114-1 and 114-2, as shown, is of equal length and the arms 114-1 and 114-2 are disposed at an angle of 60° with respect to each other. Each arm 114-1 and 114-2 includes apertures 116-1, 116-2 and 116-3, adapted to engage a screw, e.g., 118 inserted through each one of apertures 116-1 and 116-2 respectively, suitable for affixing a base 10 to a portion of a patient's mandible 112. In one embodiment, each arm 114-1 and 114-2 includes a flexible portion 110. Although the embodiment illustrated in FIGS. 2-3 show equal length arms 114-1 and 114-2 at a 60° angle, in other embodiments, the length of arms 114-1 and 114-2 are not necessarily equal and the angle of the arms 114-1 and 114-2 relative to each other may be at any acute angle, but would be most effective at a range of 45° to 90° relative to each other. In some embodiments, distal fastener portions 106 and 108 and intermediate fastener portion 104 is secured to the mandible 112 by a fastener such as an internal fixation screw, e.g., screw 118, inserted through an aperture, e.g., 116-1, 116-2, and 116-3, that is drilled or formed therein to receive a fastener such as a screw 118 in FIG. 2A, to penetrate and attach to the bone. In one embodiment, standard bone screws known to persons skilled in the art, including internal fixation screws having approximate dimensions 2.0 mm by 4 to 6 mm, may be used. It is appreciated by those skilled in the art however that a pin, nail, brad, adhesive, or other fasteners are also suitable. The base 10 may be fastened to the mandible 112 by bio-absorbable material, in which the material selected for the fasteners should be such that the fasteners will take at least as long to be absorbed by the patient's tissues as the time required for osteosynthesis. In this embodiment, each fastener portion 106 and 108 is equidistant from an intermediate fastener portion 104. However, it will be apparent to persons skilled in the art, that this is not required in other embodiments and that the fastener portions can be respectively positioned at a variety of positions along the arms 114-1 and 114-2. In use, one embodiment is implanted subcutaneously through a small incision in the skin.

In one embodiment each aperture, 116-1, 116-2 and 116-3, acts as a drill guide to enable a surgeon to accurately drill a hole into the mandible 112, and place a fastener through the fastener portions 104, 106 and 108, and into a mandible 112 without repositioning the base 10. In other embodiments, only one or two of apertures 116-1, 116-2 and 116-3 will act as drill guides.

In some embodiments, best seen in FIG. 3, apertures 116-2 and 116-3 of each fastener portion 106 and 108, contain a countersink 120-1 and 120-2, respectively, the diameter of each countersink 120-1 and 120-2 can be adapted to accept screws of any desired shape or gauge.

In some embodiments best seen in FIG. 3, the intermediate fastener portion 104 contains a shelf 132, which is sized and shaped to allow a threaded portion 128 of a screw, e.g., 118, to be slideably received by the shelf 132 such that the screw head 126 contacts with the buccal-labial surface of the shelf 132 of a base 10.

Figure 4:
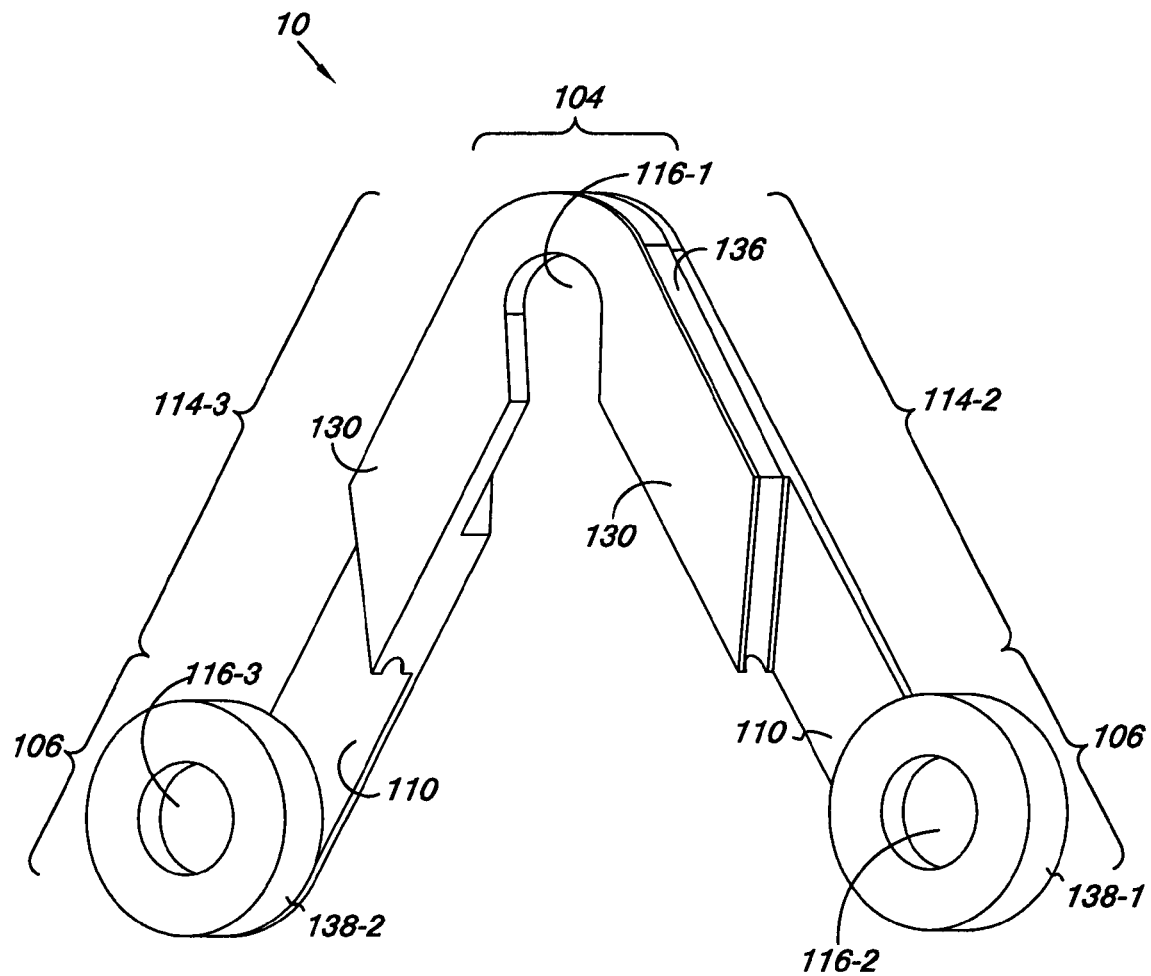
FIG. 4 is a bottom perspective view of an embodiment of the invention.
Figure 8:
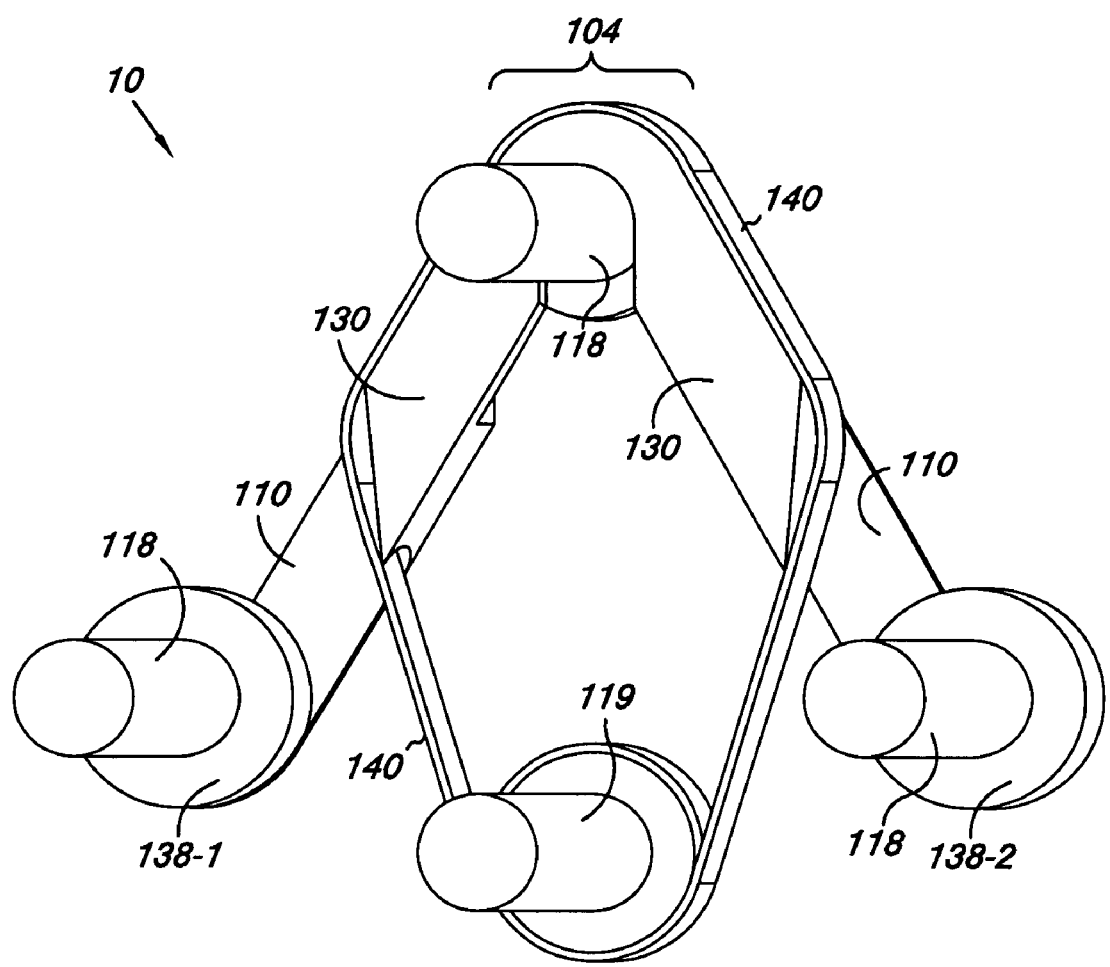
FIG. 8 is a bottom view of an embodiment of the invention shown in combination with a tension wire.
Figure 9:
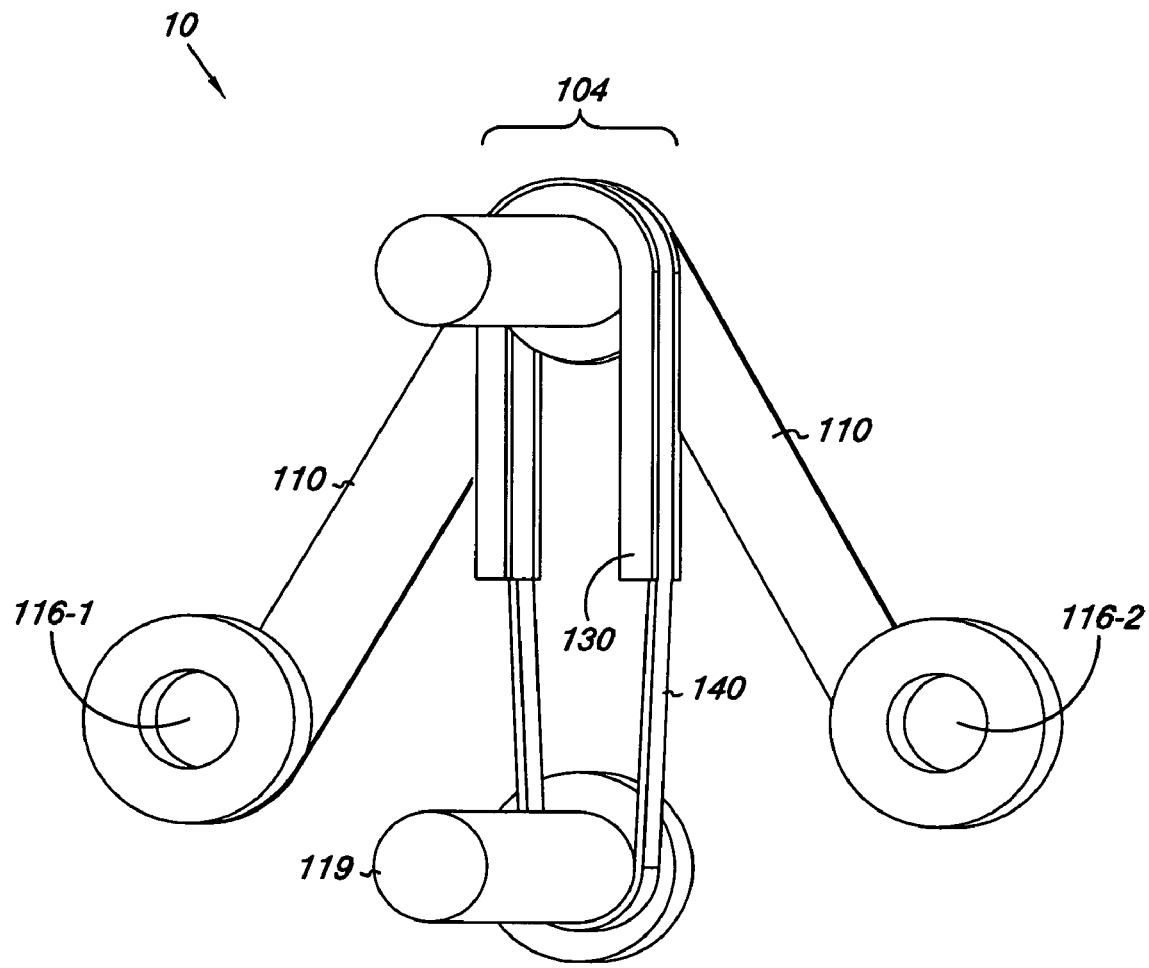
FIG. 9 a bottom view of an embodiment of the invention shown in combination with a tension wire.

Referring now to FIGS. 4, 8 and 9, the surface of an illustrated base 10, is the bone-contacting, surface because, in practice, this surface faces toward the cortical surface of the bone. These embodiments include a retainer portion 130, that contains at least one intermediate fastener portion 104, the retainer portion 130 being continuous about the intermediate fastener portion 104 and along at least a part of each arm 114-1 and 114-2. The retainer portion 130 is intended to contact the cortical surface of the mandible 112. In one embodiment, the retainer portion 130 has a substantially constant thickness over its length. In one embodiment, the thickness of the retainer portion 130 is about 0.77 mm. Those skilled in the art however, will appreciate that the thickness of the retainer portion 130 is limited only by the strength of the materials used to construct the retainer portion 130 and the patient's acceptance of the base while it remains fastened to the bone. The retainer portion 130 is substantially inflexible and it is intended to cross the fracture line 100 and provide a rigid surface to assist in reducing the opposing fragments. In practice, the surgeon will position the bone-contacting surface of retainer portion 130 such that it crosses each side of the fracture line 100, best illustrated in FIG. 10. Placing the retainer portion 130 across the fracture line 100 so that the retainer portion 130 overlaps the fracture line 100 restrains undesirable movement (displacement) in the lingual direction 94 of the fragment on the side of the fracture line 100 on which the intermediate fastener portion 104 is affixed. As a result of this overlap, the mandible fragments on opposite sides of the fracture 100 are effectively restrained against relative movement.

FIG. 9 illustrates a flexible portion 110 of each arm 114-1 and 114-2, of an embodiment of the invention. The flexible portion 110 is susceptible to being bent and is intended to bend, during fixation of the base to the mandible 112 and during osteosynthesis. This characteristic is not present in conventional plates. Conventional internal fixation plates have a thickness in the ranges of 1.5 mm to over 2.0 mm. Surgeons using a convention internal fixation plate will use an instrument to bend and twist a conventional plate e.g. 98, as illustrated in FIG. 1.

Figure 5:
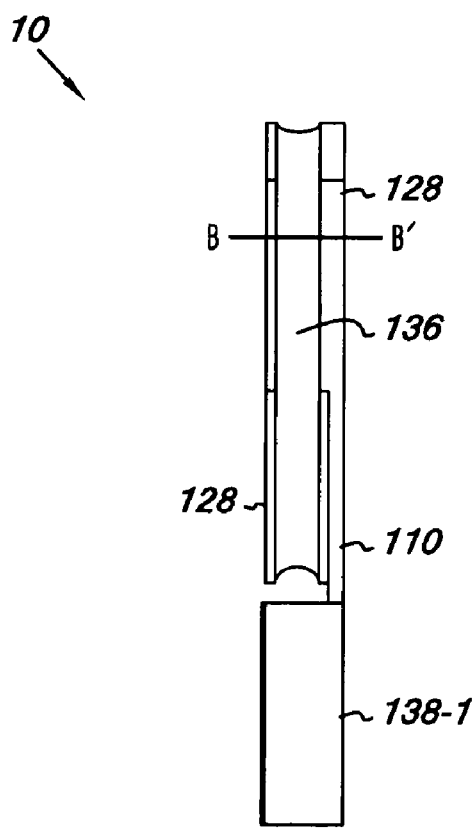
FIG. 5 is a side view of an embodiment of the invention.
Figure 6:
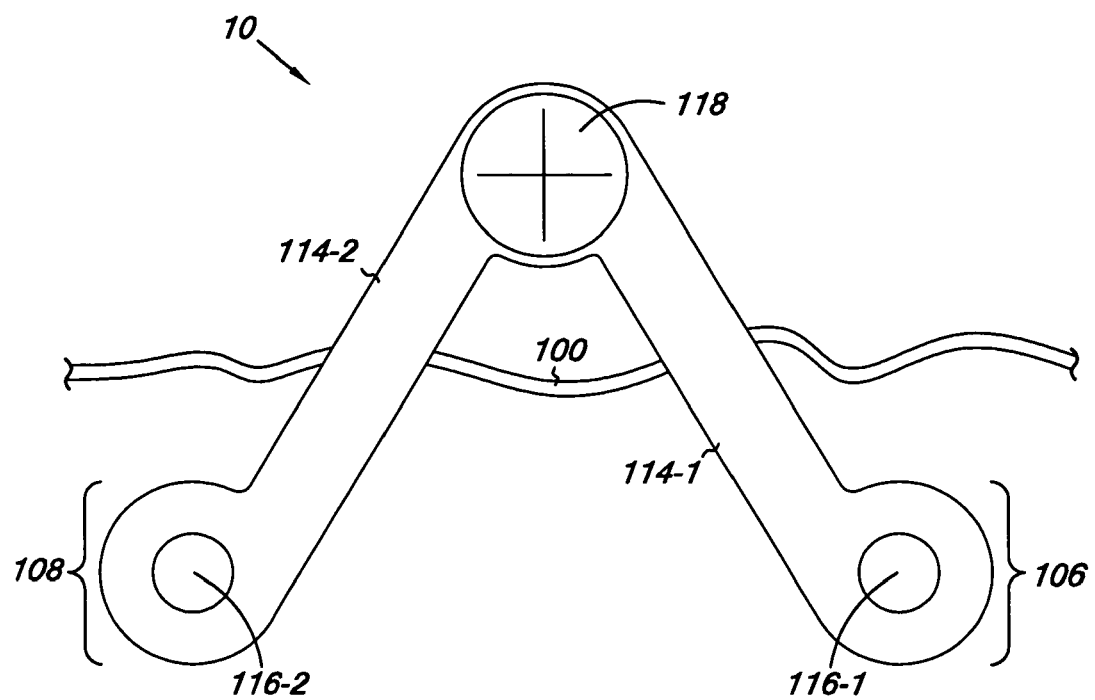
FIG. 6 is a top view of an embodiment of the invention shown across a fracture line.

In contrast, the flexible portion 110 of an internal fixation plate in accordance with one embodiment of the present invention has a thickness over its length of about 0.25 mm, preferably in the range of about 0.2 mm to about 1.0 mm, best illustrated along line B-B' in FIG. 5. This difference in thickness results in certain advantages over conventional internal fixation plates. In general, the flexibility, i.e., the amount of deflection or deformation that the flexible portion 110 will undergo as a result of a force (F) placed upon it, can be analyzed in accordance with the following equation:

$$\delta = \frac{FL^3}{3E\frac{wh^3}{12}} = \frac{4FL^3}{Ewh^3}$$

is deflection
where
$\delta$ is the width of the arm,
E is the Young's modulus of elasticity of the material of the flexible portion,
F is the amount of normal force exerted when tightening the screw,
H is the thickness of the flexible portion (or another lever) and,
L is the length of the arm.

Comparing the measure of flexibility (deflection) for flexible portion 110 with a conventional internal fixation plate with a thickness of 1.5 mm may be useful. Assuming that internal fixation plates are constructed of the same materials, i.e., stainless steel or titanium, the above equation shows that the flexible portion 110 on one embodiment of the proposed invention will be 216 times more flexible than a base of 1.5 mm thickness. Surgeons using a device in accordance with an embodiment of the present invention will notice this difference between the force required to flex the flexible portion 110 of base 10 and the force required to flex a convention internal fixation plate.

Figure 7:
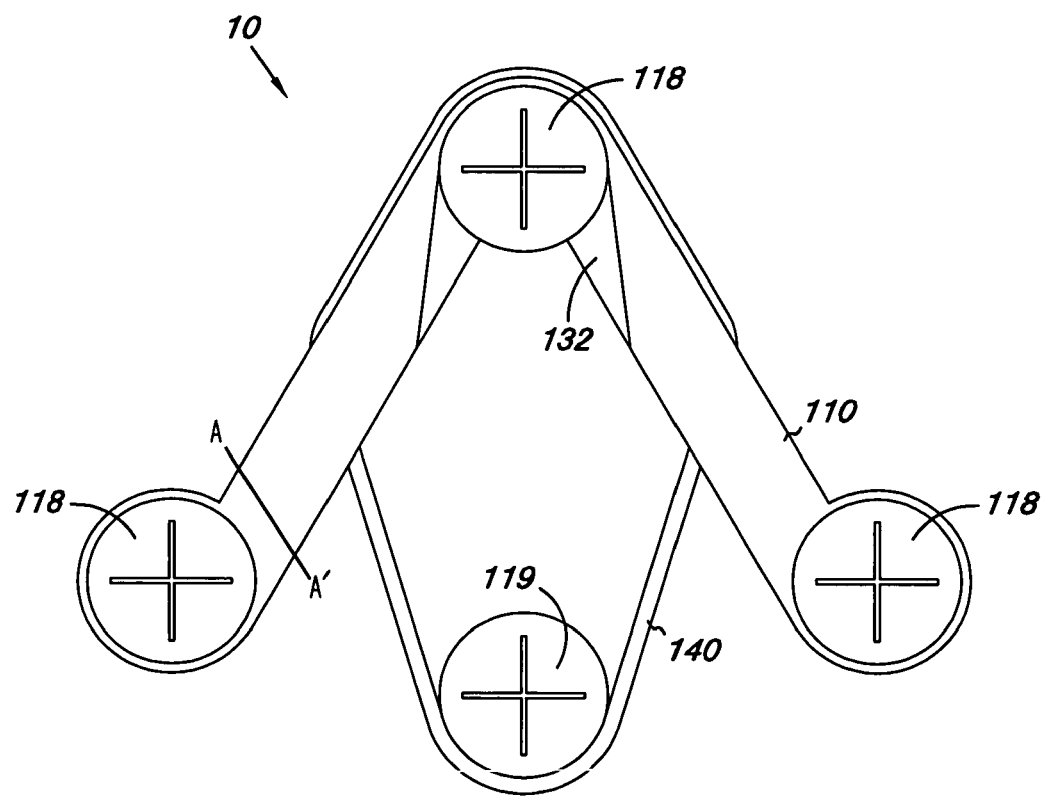
FIG. 7 is a top view of an embodiment of the invention shown in combination with a tension wire.

The flexible portion 110 of an internal fixation plate in accordance with one embodiment of the present invention has width (w) of about 2.25 mm, best illustrated along line A-A' in FIG. 7, and the length of the arm (L) is in the range of 6 to 15 mm, best illustrated along line C-C' in FIG. 2. Other embodiments will have differing dimensions for the flexible portion 110 such as from about 0.20 to 1.0 mm in thickness.

One advantage with some embodiments of the present invention is that little or no bending will occur in the retainer portion 128 relative to the bending that will occur in the flexible portion 110. The flexibility of flexible portion 110 has the additional advantage in that it eliminates the difficulty encountered with prior metal internal fixation plates when, during surgery, the surgeon attempts to bend and shape a plate, e.g., plate 98 of FIG. 1, to conform to the surface of the bone. The increased flexibility of flexible portion 110 is also particularly advantageous in that this, flexibility allows the base 10 to conform to the contours of the mandible 112 during osteosynthesis, thereby ensuring that unwanted bone deformation does not occur. Another advantage of some embodiments, is that its low profile or thickness, as measured from the buccal-labial surface to the bone-contacting surface of about 1.37 mm, allows the plate to be left permanently in the patient. In other embodiments, the thickness range from about 1.1 mm to 1.5 mm. In considering thickness, a primary concern is acceptance by the patient.

Figure 4A:
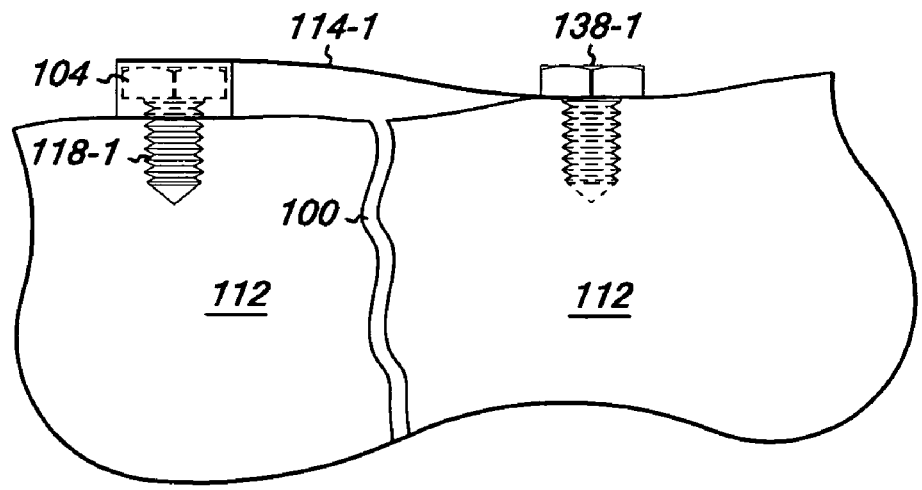
FIG. 4A is a side view of an arm of an embodiment of the invention.

Turning again to FIGS. 3 and 4, in one embodiment, collars 138-1 and 138-2 are disposed at a distal end of each arm 114-1 and 114-2 of the flexible portion 110. The collars 138-1 and 138-2, are of about equal thickness 1.37 mm, relative to the retainer portion 130. In one embodiment, best shown in FIG. 3, an end of the flexible portion 110 terminates on the buccal-labial surface of a base 10. However, persons skilled in the art will appreciate that the flexible portion 110 could also terminate on the cortical contacting surface, best seen in FIG. 4A, or, at any place along a collar 138-1 and 138-2. In still other embodiments, collars 138-1 and 138-2 are not required. In other embodiments (not shown), arms 114-1 and 114-2 include a fastener portion 106, 108, along their lengths instead of at the distal end of the arm.

In one embodiment, as shown in FIGS. 4, 5, and 7, a base 10 contains a wire channel or groove 136 that extends around the periphery of the rear of the base 10 and serves as a tension member receiving means to accept a tension member such as a wire 140, that is used during a surgical procedure in which a surgeon desires to use the Tension Wire Method (TWM) of fixating the bone fragments. The term "tension wire" is used herein as a matter of convenience only. Any means for reducing the fracture is suitable. In another embodiment, the tension wire 140 is enclosed into base 10 while in other embodiments, the wire channel or groove is shaped in such a manner, e.g., a quarter circle, or by any other means, that forces the tension wire 140 to remain flush with the surface of the bone. The method of using the base 10 in conjunction with the TWM method will be explained in detail below.

Conventional linear plates function best when placed normal to the fracture line. In this orientation, the length of the linear plate performs like a beam with fully fixed ends. The finite element analysis of a device in accordance with an embodiment of the invention demonstrated that such a device withstands the stresses, including mastication, exerted during osteosynthesis. That is, stresses on an embodiment of the base, were well below the stresses that would produce deformation or failure in the various components of the device. One advantage, therefore of using a device in accordance with the present invention, is that the surgeon can choose an internal fixation base having flexibility without sacrificing the strength required to fix the fragments against the forces of mastication.

Figure 11:
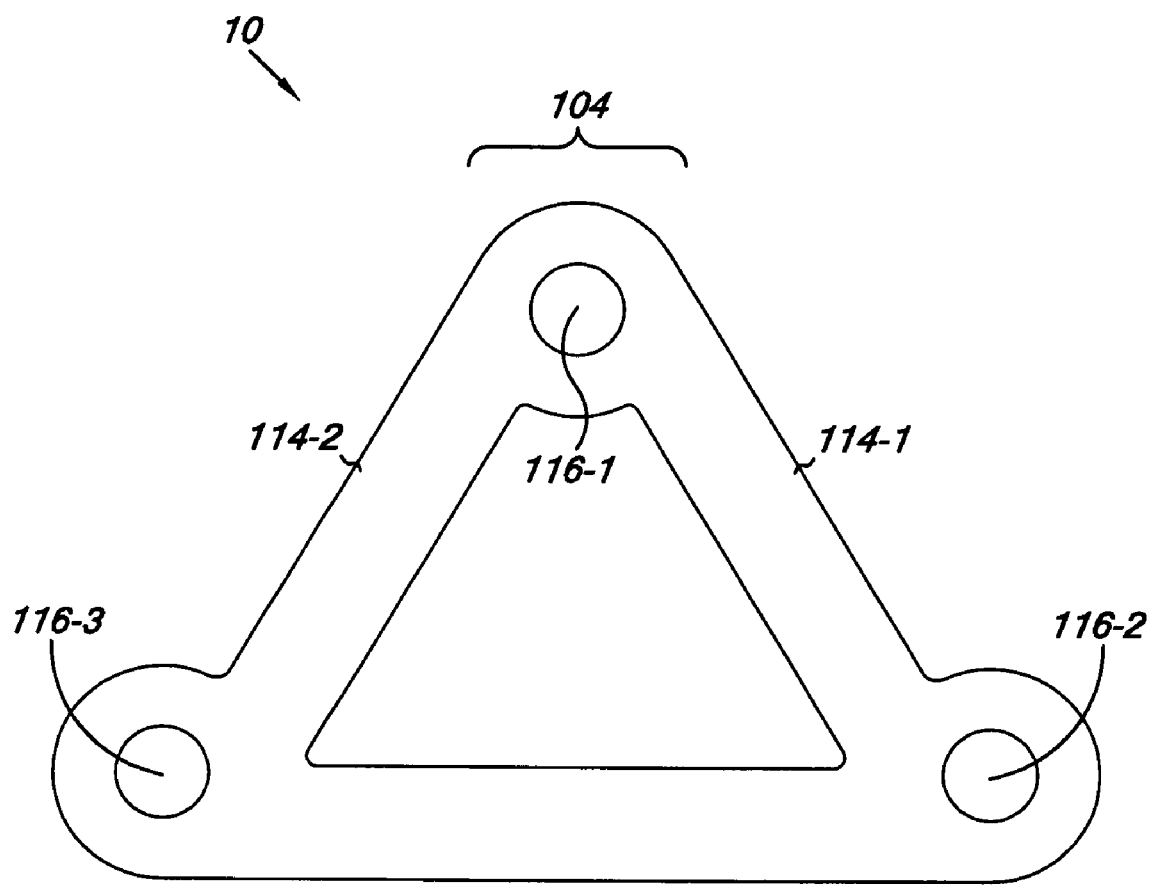
FIG. 11 illustrates an embodiment of the invention.
Figure 11A:
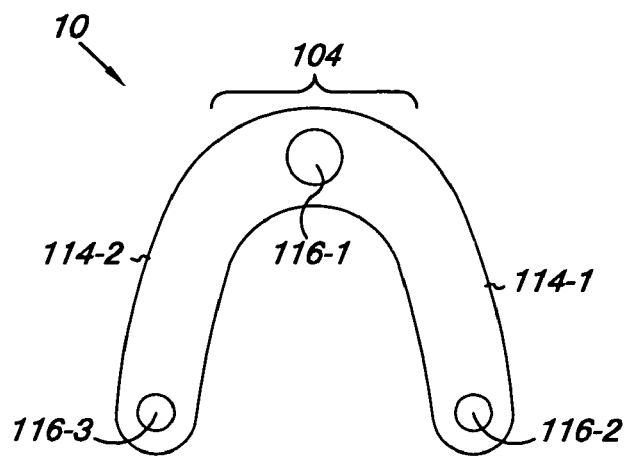
FIG. 11A illustrates an embodiment of the invention.
Figure 11B:
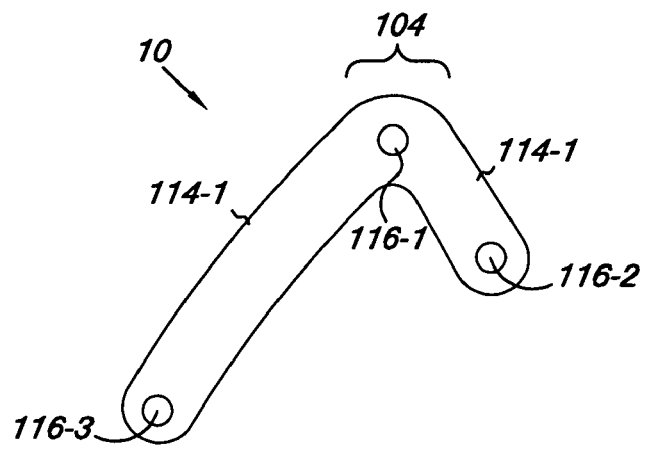
FIG. 11B illustrates an embodiment of the invention.
Figure 11C:
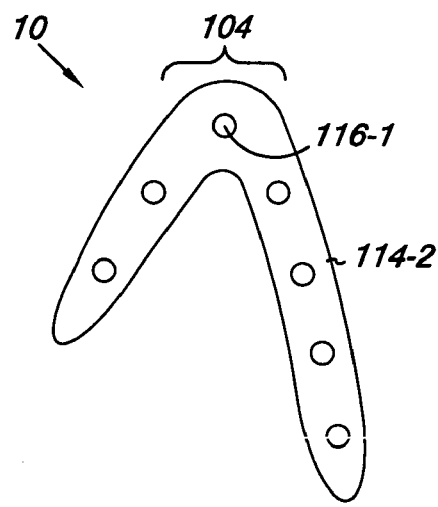
FIG. 11C illustrates an embodiment of the invention.

A device in accordance with embodiments of the present invention may be made in full or in part from any appropriate bio-compatible material such as titanium or stainless-steel. The fasteners may also be comprised of any bio-compatible material, as long as the material selected for the screws is such that the screws will take at least as long to be absorbed by the patient's body as the time necessary for healing of the fracture. It will be appreciated by those skilled in the art, however, that other materials having suitable performance and biocompatibility characteristics may be used in other embodiments. Although an embodiment of the invention has been described with respect to a v-shaped base, other embodiments can use bases or plates of other shapes. For instance, FIG. 11 shows a triangle shaped base, while FIG. 11A shows a "U" shaped base, FIG. 11B a base with arms of unequal length, and FIG. 11C a base with more than three attachment locations. Each shape may be suitable for embodiments of the invention. As will be understood by persons skilled in the art, shapes other than those shown will also be suitable for various embodiments of the invention.

Figure 10:
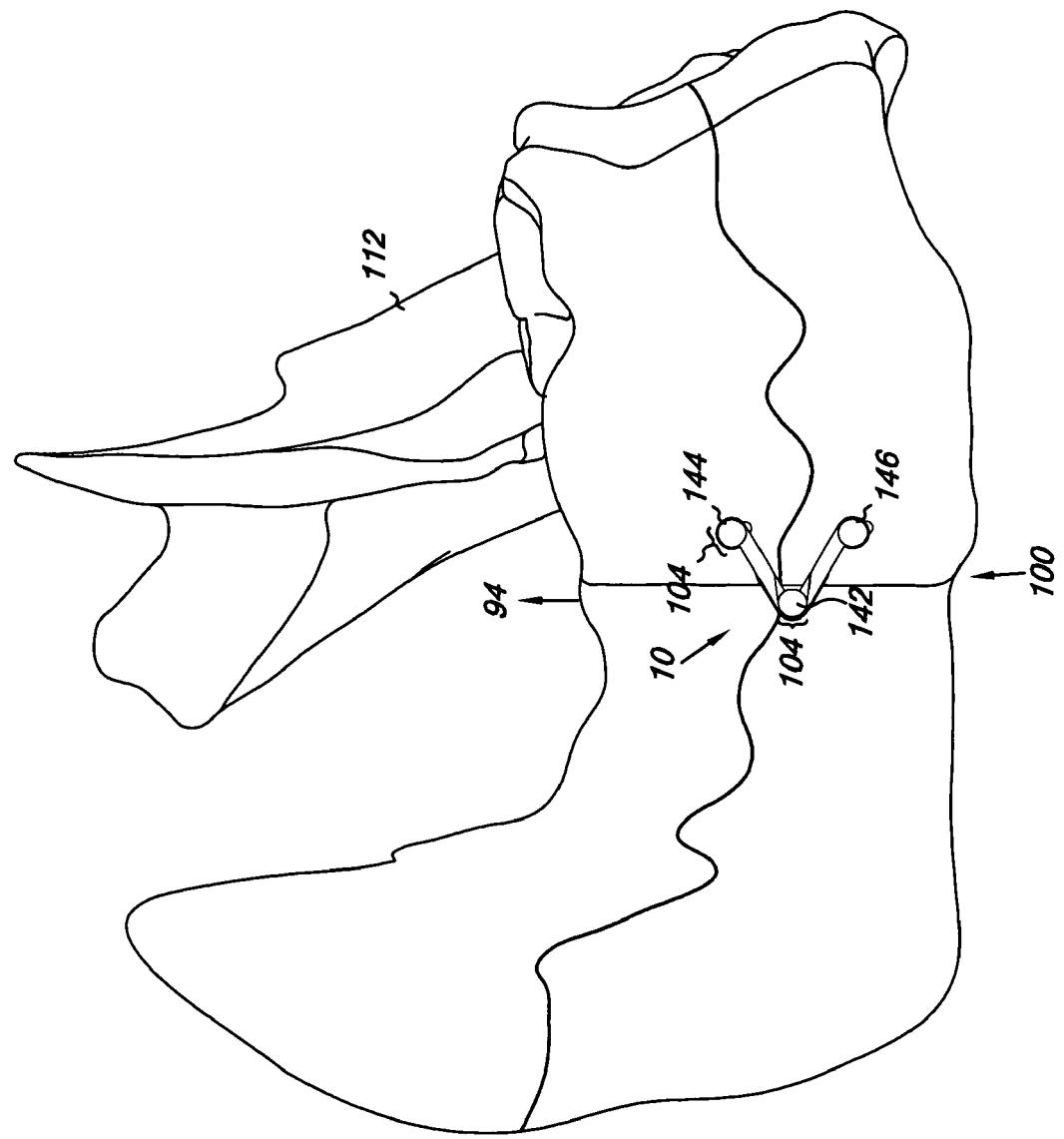
FIG. 10 is a 3-dimensional view of a mandible with an embodiment of the invention.

A method for treating a fracture of the mandible on a patient according to the present invention comprises the following steps. Referring now to FIG. 10, an incision is made and dissection performed (not shown) for access to the fracture line 100. The side of the fracture line on which there is greater lingual displacement is located and a first hole 142 is drilled normal to, and about 4 to 6 mm from, the fracture line 100. A first screw, e.g., 118, is inserted through an aperture, e.g., 116-1, in the intermediate fastener portion 104 and into the first hole 142 drilled into the bone. Grasping the base 10, the surgeon orients each arm 114-1 and 114-2 in such a manner that the retainer portion 130 of base 10 crosses the fracture line 100. The first screw is tightened thereby affixing the intermediate fastener portion 104 to one side of a fracture line 100 and reducing the relative buccal-labial displacement of the mandibular bone on the side opposite to intermediate fastener portion 104. After satisfactory reduction is assured, an aperture, e.g., 116-1, is used as a guide to drill a second hole into the mandible, and a second screw, e.g., 118, is placed into the second hole 144 just drilled with the screw so placed then tightened. This procedure of drilling holes and placing screws is repeated for a third hole 146. In some embodiments having more than three apertures, the procedure of drilling and placing screw is repeated for as many screws as desired.

Figure 10A:
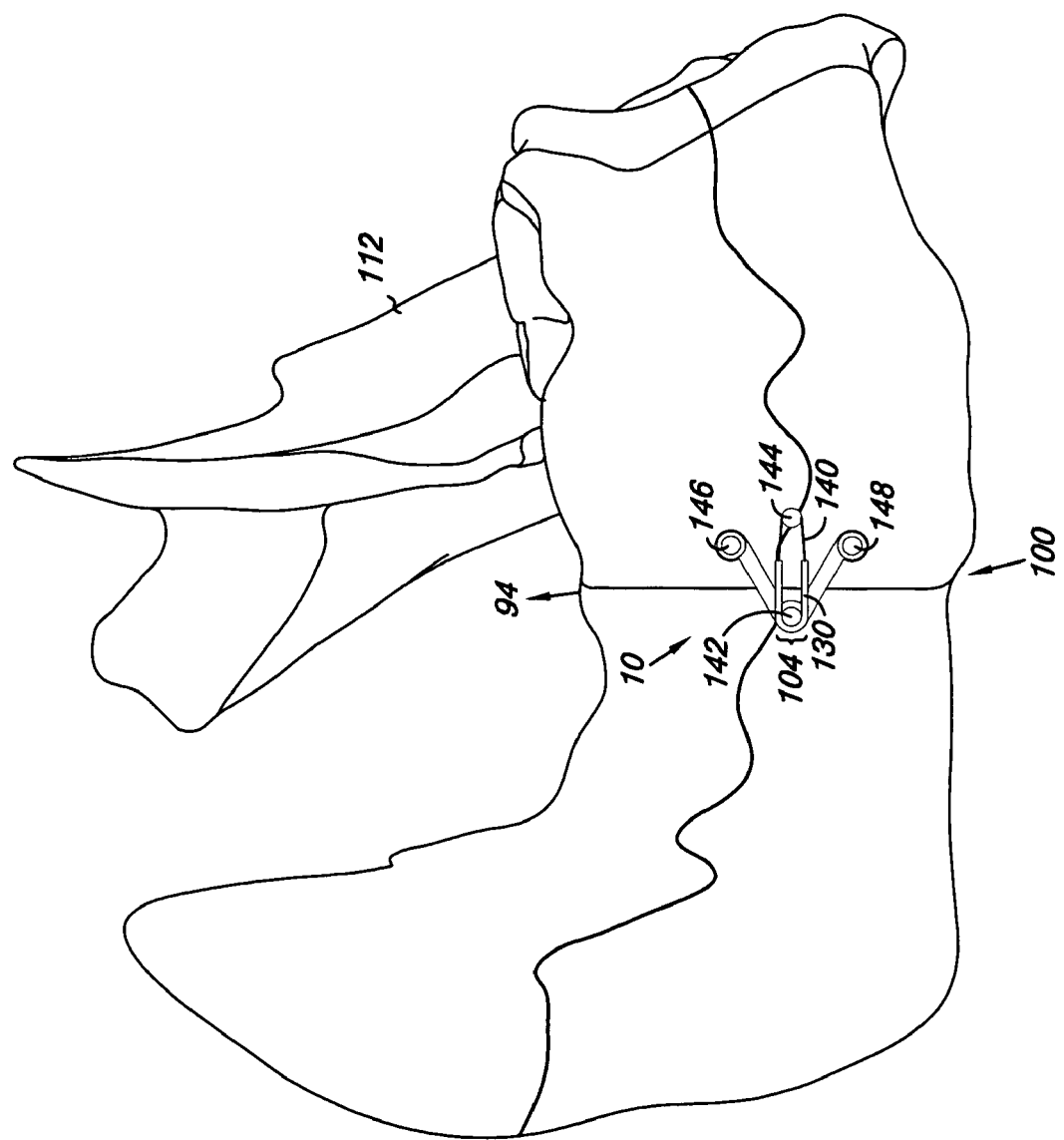
FIG. 10A is a 3-dimensional view of a mandible with an embodiment of the invention shown in combination with a tension wire.

Turning now to FIG. 10A, a device according to an embodiment of the present invention may also be used in combination with the tension wire method (TWM). A method for treating a fracture of the mandible on a patient according to an embodiment of the present invention using TWM, comprises the following steps: An incision and exposure (not shown) is made for access to the fracture site. The side of the fracture line on which there is greater lingual displacement is located and a first hole 142 and a second hole 144 are drilled normal to and about 4 to 6 mm from the fracture line 100. A first screw e.g., 118 is placed in the first hole 142 in the mandible and a tension post 119, which may be a second screw, is placed into the second hole 144 in the mandible, both screws are tightened and both screws are reversed about two turns. A bone-contacting surface of the retainer portion 130 of an embodiment containing a wire channel 136, best seen in FIGS. 3, 4 and 5, is inserted under the screw head 126 of the screw placed on the side of the fracture with lesser buccal-labial displacement relative to the opposing fragment, thereby slideably engaging the shelf 132 with the screw head 126 of the first screw so that the retainer portion 130 crosses the fracture line 100. The first screw is then tightened onto the shelf 132 thereby affixing a base 10 to one side of the fracture line 100. A tension means, which may be a wire 140, is then placed around wire channel or groove 136 of base 10 and also around the second screw. The surgeon then tightens the tension wire 140 around the wire channel 136 and the second screw. By tightening the tension wire 140, and the second screw, the surgeon properly reduces and fixates the fragments of the fracture simultaneously and orients base 10 in such a manner that the retainer portion 130 of the base 10 crosses the fracture line 100. Using apertures 116-2 and 116-3, in fastener portions 106 and 108 respectively, that have been placed over the same side of the fracture on which the second screw was placed as guides, the surgeon then drills holes through each of the apertures 116-2 and 116-3 and inserts, respectively, a third screw and a fourth screw through each one of the apertures 116-2 and 116-3 and tightens the third and fourth screws to permanently affix a base 10 to the patient's mandible. The hole for the first fastener portion is drilled and the first screw placed before the next hole is made and the next screw placed. In embodiments having more than three apertures, this procedure of drilling holes and placing screws is repeated for as many screws as is desired.

It should be understood that the particular embodiments described above are only illustrative of the principles of the present invention, and various modification could be made by those skilled in the art without departing from the scope and spirit of the invention, thus, the scope of the present invention is limited only by the claims that follow.

We claim:
1. A method of repairing a fracture in a bone, comprising:
   making an incision to expose the bone;
   identifying the fractured portion of the bone;
   applying a base to a surface of the bone, the base having first and second arms forming an acute angle, first and second attachment locations at distal portions of the first and second arms, and a third attachment location intermediate the first and second attachment locations, wherein the first and second arms have portions proximal to the distal attachment locations which are sufficiently flexible to allow the first and second arms to conform to the surface of the bone when the attachment locations are secured to the bone, the base having a rigid retainer portion extending outwardly from the base transverse to the fracture;
   securing the third attachment location to the bone on a first side of the fracture;
   securing the first and second attachment locations to the bone on an opposing side of the fracture; and,
   securing the attachment locations sufficiently to cause the retainer portion to engage the fracture to preclude movement of the fracture portions normal to the retainer portion.

* * * * *